(12) United States Patent
McGuinness

(10) Patent No.: US 6,350,279 B1
(45) Date of Patent: Feb. 26, 2002

(54) ENDOLUMINAL STENTS AND THEIR MANUFACTURE

(75) Inventor: Colm P. McGuinness, Galway (IE)

(73) Assignee: AVE Connaught, Dublin (IE)

(*) Notice: Subject to any disclaimer, the term of this patent is extended or adjusted under 35 U.S.C. 154(b) by 0 days.

(21) Appl. No.: 09/592,763

(22) Filed: Jun. 13, 2000

Related U.S. Application Data

(62) Division of application No. 09/013,674, filed on Jan. 26, 1998, now Pat. No. 6,102,943.

(51) Int. Cl.[7] .................................................. A61F 2/06
(52) U.S. Cl. ...................................... 623/1.12; 623/1.15
(58) Field of Search .............................. 623/1.11, 1.14, 623/1.15, 1.16, 1.18, 1.2; 606/194, 198; 128/898; 29/592.1

(56) References Cited

U.S. PATENT DOCUMENTS

| | | | |
|---|---|---|---|
| 4,502,159 A | * 3/1985 | Woodroof et al. ............... 3/1.4 |
| 4,740,207 A | 4/1988 | Kreamer | |
| 5,192,307 A | 3/1993 | Wall | |
| 5,441,515 A | * 8/1995 | Khosravi et al. ............ 606/194 |
| 5,443,500 A | 8/1995 | Sigwart | |
| 5,540,713 A | 7/1996 | Schnepp-Pesch et al. | |
| 5,591,197 A | * 1/1997 | Orth et al. .................... 606/198 |
| 5,707,386 A | 1/1998 | Schnepp-Pesch et al. | |
| 5,766,239 A | * 6/1998 | Cox ................................ 623/1 |
| 5,836,964 A | 11/1998 | Richter et al. | |
| 5,876,419 A | * 3/1999 | Carpenter et al. ........... 606/198 |
| RE36,327 E | 10/1999 | Kreamer | |
| 6,042,605 A | * 3/2000 | Martin et al. ................... 623/1 |

FOREIGN PATENT DOCUMENTS

| | | |
|---|---|---|
| EP | 0709067 | 5/1996 |
| EP | 0732089 | 9/1996 |
| EP | 0770365 | 5/1997 |
| WO | WO 94/21196 | 9/1994 |
| WO | WO 97/37617 | 10/1997 |

* cited by examiner

*Primary Examiner*—Corrine McDermott
*Assistant Examiner*—Hien Phan
(74) *Attorney, Agent, or Firm*—Sterne, Kessler, Goldstein & Fox P.L.L.C.

(57) ABSTRACT

Tubular stents are formed from a sheet of material having longitudinally extending margins and an expandable pattern between the margins. The sheet can be formed to a tube with the margins overlapped and secured. The margins may be provided with means to facilitate registration of the margins.

4 Claims, 5 Drawing Sheets

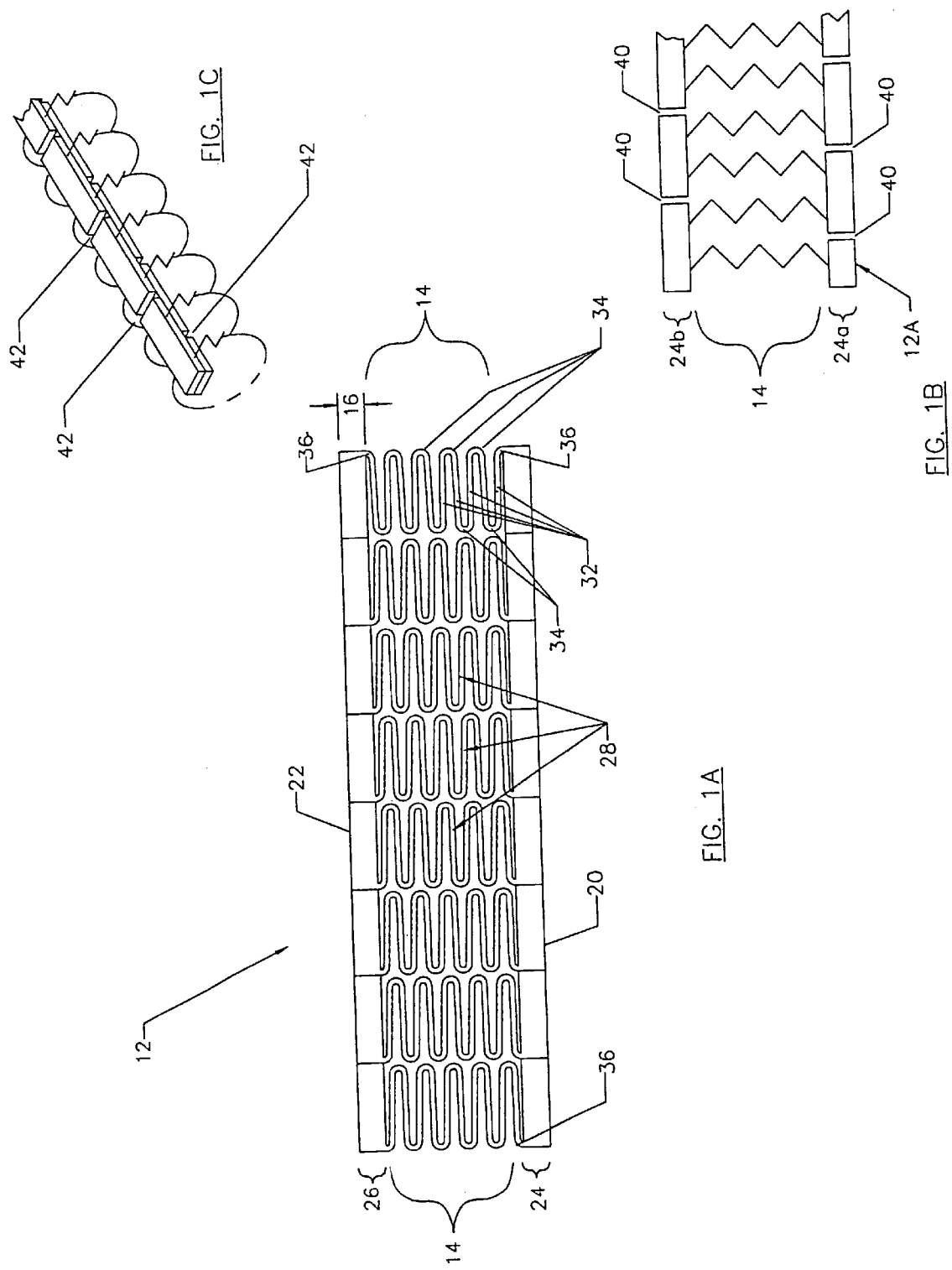

ENDOLUMINAL STENTS AND THEIR MANUFACTURE

This application is a division of U.S. App. Ser. No. 09/013,674, filed Jan. 26, 1998, now U.S. Pat. No. 6,102,943.

FIELD OF THE INVENTION

This invention relates to endoluminal stents and techniques for their manufacture.

BACKGROUND OF THE INVENTION

Recent years have witnessed increased development and use of stents, particularly those adapted for use in body lumens such as blood vessels, urological passages and biliary passageways. Stents have found increasing use as an adjunct to angioplasty, a technique in which an obstructed blood vessel is dilated, as by use of a lob balloon dilatation catheter. Although angioplasty has proved to be highly effective in the treatment of arterial obstructions, a substantial number of cases result in restenosis, that is, a tendency for the obstruction to reestablish itself. By placing a stent within the dilated region of the blood vessel, the prospects for avoiding post-procedure luminal obstruction are considered to be substantially improved.

Stents typically may be considered as defining a generally tubular structure that is adapted to be maintained in a small diameter (low profile) and expanded to a larger diameter. The low profile facilitates its advancement through and placement at the desired site in the blood vessel where it then can be expanded to the larger diameter, configuration in which it is in firm engagement with the inner lumen of the vessel and can serve as a scaffold to maintain that portion of the vessel open. Among the different types of stents are those that are self-expanding under their inherent resilience, those that are expandable by a trigger mechanism, such as by making the stent from a shape memory alloy and then heat activating the alloy to its expanded configuration, and balloon-expandable stents in which the stent is expanded by an inflatable balloon from its low profile to its expanded, deployed configuration. Regardless of the type of stent, its delivery device typically is removed after the stent has been expanded and deployed.

In many applications that lend themselves to use of a stent, the body lumen is quite small and the stent similarly must be correspondingly small. For example, stent adapted for placement in a coronary artery may have an initial low profile diameter as small as 1.5 millimeter and may be expanded to a diameter of up to about 3.5 millimeter or more. The stent, which may be formed from an arrangement of wires, cut or etched tubes, or other configurations may be considered as having a wall thickness of the order of 1 millimeter or less. Numerous structural configurations may be employed including various arrangements of struts, zigzag members and flat sheets rolled into tubes, among others. Among the important objectives in the design and manufacture of a stent is that the stent should be capable of assembly and fabrication with a minimum of difficulty. That objective can be challenging particularly with small stents in which it may be difficult to assemble or align the individual components.

For those stents that are formed from a continuous, unitary material, such as a metal tube or sheet, the stent pattern may be formed by a variety of techniques, including the use of laser cutting and photochemical etching, among others. The prior art describes techniques for forming a balloon expandable metal stent from a tube by cutting slits in the tube (e.g., Palmaz U.S. Pat. No. 4,773,655), by laser cutting defined patterns in such a tube (e.g., International application PCT/US96/02615) or by photochemically etching (e.g., Lau, U.S. Pat. No. 5,421,955). U.S. Pat. No. 4,680,031 discloses a tubular stent adapted for use with a heart valve in which the stent is formed from a flat metallic sheet in a predetermined pattern, such as by chemical etching, with the sheet then being rolled into a tubular shape and its edges secured to each other as by welding.

The fabrication of the stent pattern in a flat sheet and then rolling the patterned sheet into a tubular stent form may have advantages over forming the stent pattern directly in a tubular member. Some difficulty, however, may be encountered when forming the patterned flat sheet into a tubular configuration and then securing the longitudinal edges of the sheet together to form the tube. With a tube so made, the longitudinal margins or edges must be properly aligned and effectively secured. In many cases, it may be desirable that the wall thickness of the stent be uniform and not substantially greater than that of the sheet from which the tube is made. That can present assembly difficulties, particularly for smaller dimensioned stents.

Among the advantages of fabricating the stent in a photochemical etching procedure is that intricate patterns, essentially of any configuration, can be formed with a high degree of precision. The precision may be considered to be greater than that achievable with direct laser cutting alone because of practical limitations on the diameter of the laser beam necessary to have sufficient power to effect the cutting. A hybrid technique is described in U.S. Pat. No. 5,421,955 in which a tube is coated exteriorly with an etchant-resistant coating that is selectively removed in a desired pattern by a laser beam. The tube then is filled with wax and is exposed exteriorly to the etchant. Because the etchant is applied only to the outside of the tube, there may be some uncertainty as to the internal configuration and dimension of the pattern on the inner surface of the tube. That may result in a lack of uniformity and predictability in the function and operation of the stent. In contrast, when forming a stent from a flat sheet, the identical pattern can be provided, in registry, on both sides of the sheet and the etching can take place simultaneously from both sides of the sheet, thereby assuring that the pattern and dimensions of the pattern on the inner and the outer surfaces of the ultimately formed stent will be essentially identical.

It would be desirable to provide a stent construction and technique for facilitating assembly of tubular stents from a flat sheet of material and in which the alignment, registration and connection between the longitudinal margins of the stent is true, secure and is effected in a simplified technique.

SUMMARY OF THE INVENTION

In practicing the invention, a tubular stent is formed from a sheet of material that has been coated, on both sides, with an etchant-resistant coating that defines the pattern of the stent to be formed. The sheet then is exposed to a chemical etchant to remove the exposed material. The etchant-resistant coating then is removed and the sheet is rolled into a cylinder in which the longitudinal edges of the rolled sheet are aligned and secured. In accordance with the invention, the longitudinal marginal edges are configured to engage each other easily and can be secured while so engaged. The marginal edges may be configured to interlock in a manner that will assure precise registration of the edges and the formation of a true cylindrical stent. The engaging portions of the margins along the longitudinal edges of the stent may be formed with various patterns to facilitate engagement and proper registration of the margins.

It is among the objects of the invention to provide a stent and technique for its manufacture that can be formed using conventional photochemical etching techniques that can be accurately assembled from a flat sheet into a cylindrical configuration; that can be rolled into a cylindrical configuration with its longitudinal margins being securely and accurately engaged; and can be made in any pattern, including multiple connected modules.

DESCRIPTION OF THE DRAWINGS

The foregoing and other objects and advantages of the invention will be appreciated more fully from the following further description thereof, with reference to the accompanying drawings wherein:

FIG. 1A is a plan illustration of a flat sheet formed to include a stent pattern before being rolled into the tubular configuration as shown in FIG. 1;

FIG. 1B is a diagrammatic illustration of the flat sheet stent pattern similar to that of FIG. 1A in which the longitudinal margins of the sheet embody a modified configuration;

FIG. 1C is a diagrammatic illustration of the sheet of FIG. 1B rolled into a tubular stent;

DESCRIPTION OF THE ILLUSTRATIVE EMBODIMENTS

Figure 1:
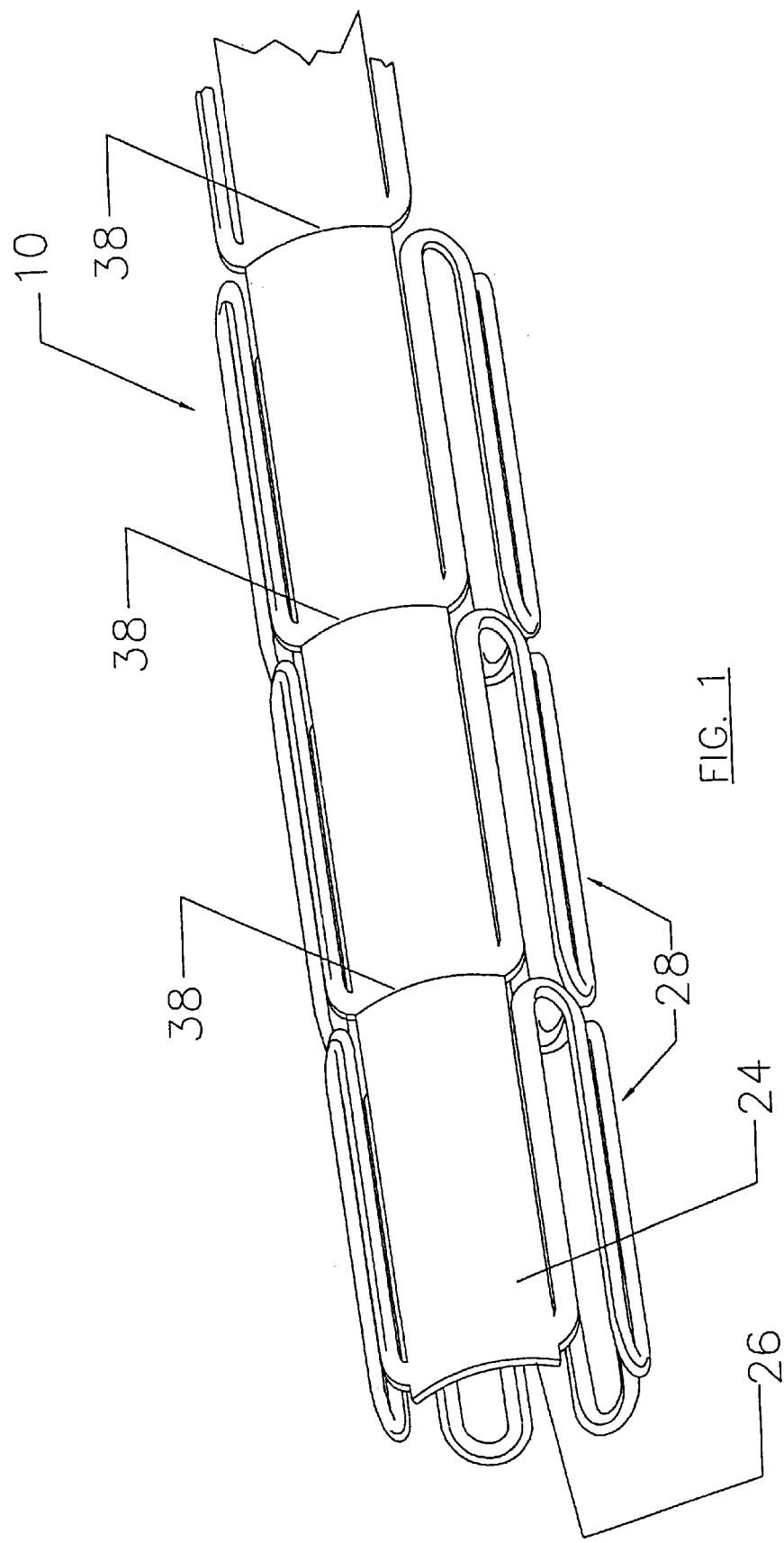
FIG. 1 is an isometric diagrammatic illustration of one embodiment of the tubular stent made in accordance with the invention.

FIG. 1 illustrates a tubular stent 10 after having been rolled into its cylindrical configuration from the flat configuration as shown in FIG. 1A. The stent 10 is tubular, having open ends and a cylindrical wall. The tubular stent is formed from a flat sheet 12 of suitable material, typically a metal such as stainless steel, that has been formed to a selected pattern of interconnected elements such as struts, legs, rods and the like of various shapes, lengths and orientation adapted to enable the cylindrical stent to be expanded, as by a balloon, from a low profile to an enlarged diameter configuration. The region of the pattern is designated generically by the numeral 14 in FIG. 1A. It should be understood that the invention may be practiced with any desired pattern that can be formed in a sheet of suitable material. The sheet 12 may be considered as having an inner surface that will define the inwardly facing surface of the tube and an opposite, outwardly facing surface. By way of example, in the embodiment illustrated in FIGS. 1 and 1A, the sheet may be formed from stainless steel (type 316) having a thickness on the order of 0.10 millimeter. The sheet is elongate, and may be considered to have a pair of longitudinal edges 20, 22 that extend the length of the sheet 12. The sheet may be about eighteen millimeters long. The sheet is treated, preferably by chemical etching, to form the configuration of the desired pattern of expandable members 28, one of which is shown in FIG. 1A as a plurality of zigzag elements. The sheet is formed to include elongate marginal segments 24, 26 formed along the longitudinal edges 20, 22 and expandable members 28 extending between marginal segments 24, 26. The marginal segments 24, 26, by way of example, may have width 16 of the order of 0.5 millimeter. Although the expandable members 28 are illustrated in FIGS. 1 and 1A as being in an irregular sinusoidal pattern, it should be understood that the patterns and geometries of the expandable members may be varied widely provided that they are arranged to enable the elements to expand in accordion-like fashion from a low profile to an expanded diameter when the sheet 12 is in its tubular stent configuration. As shown, the flat sheet 12 is formed to define a series of expandable members 28 formed as zigzag arrays, each defined by serially connected alternating legs 32 and bends 34. By way of example, the cross-section of the legs 32 and bends 34 may be generally rectangular, having a thickness of 0.10 millimeter (the thickness of sheet 12) and a width of 0.15 millimeter. The endmost arrays are connected to the ends of the marginal segments 24, 26, as indicated at 36. That may necessitate reversal of the zigzag sense of one of the endmost expandable members 28.

The sheet 12, so formed, may be formed into a cylindrical configuration in which the marginal segments 24, 26 overlap each other, as suggested in FIG. 1. The marginal segments 24, 26 are secured to each other by any of a variety of techniques, such as laser welding, adhesive bonding, or other suitable techniques. The resulting structure thus may be considered as defining an elongate spine defined by the overlapping marginal segments 24, 26 and a plurality of serially located radially hoop-like expandable members 28. Should it be desired to increase the longitudinal flexibility of the spine, marginal segments 24, 26 may be provided with selectively located weakened regions 38. The weakened regions 38 may be located along those portions of the marginal segments 24, 26 that are located between adjacent expandable members 28. By way of example, the weakened regions may be formed by etching or otherwise forming a line, for example, of the order of 0.001 to 0.002 inch deep.

The weakened regions should be formed on that surface of the marginal segments 24, 26 that face outwardly when the sheet 12 has been assembled in the tubular stent configuration. Among the advantages of the stent is that the spine will maintain the length of the stent when the stent is expanded.

FIG. 1B illustrates a modified version of the embodiment of FIGS. 1 and 1A in which the marginal segments 24a, 26a are provided with gaps 40 so that the margins 24a, 26a are interrupted. The gaps preferably are located on their respective margins so that they are staggered, that is, a gap 40 on one margin (e.g. 24a) will not align with a gap 40 on the opposite margin (e.g., 26a) when the sheet 12a is rolled into a cylindrical form. Consequently, when the sheet is rolled into a tubular form as suggested in FIG. 1C, the composite spine will be defined by a plurality of longitudinally spaced hinge regions 42, each defined by the thickness of the sheet from which the device is formed.

Figure 2:
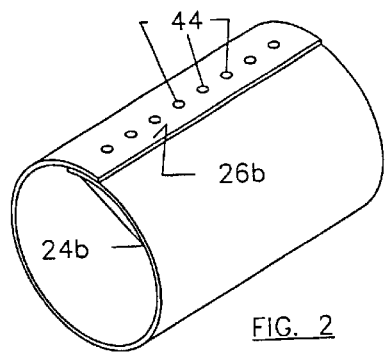
FIG. 2 is an isometric diagrammatic illustration of a modified form of assembled cylindrical stent formed from an initially flat sheet in which the longitudinal margins of the sheet are pinned to each other with rivets.
Figure 2A:
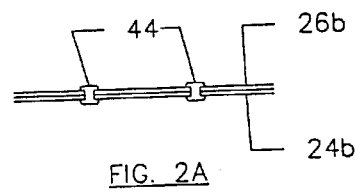
FIG. 2A is a longitudinal sectional illustration as seen along the line of rivets of FIG. 2.

FIG. 2 illustrates a modified embodiment of the invention in which the overlapped margins 24b, 26b may be secured to each other, at least in part, by a plurality of pins or rivets 44. The rivets 44 preferably are radiopaque and may be made from an appropriate material, such as a gold alloy or other suitable radiopaque alloy. In FIG. 2, the cylindrical wall of the stent omits the radially expandable elements, for ease of explanation.

Figure 3:
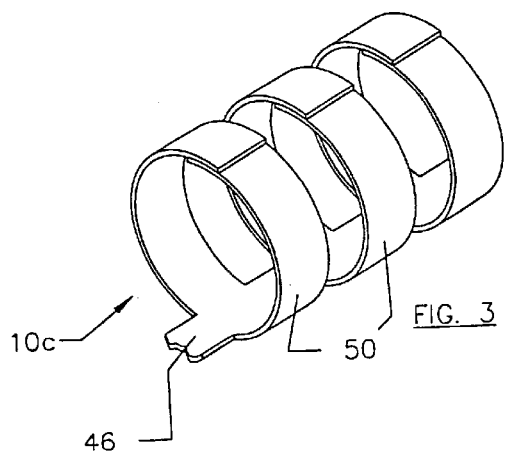
FIG. 3 is a diagrammatic illustration of another embodiment of a cylindrical stent formed from a flat sheet.
Figure 3A:
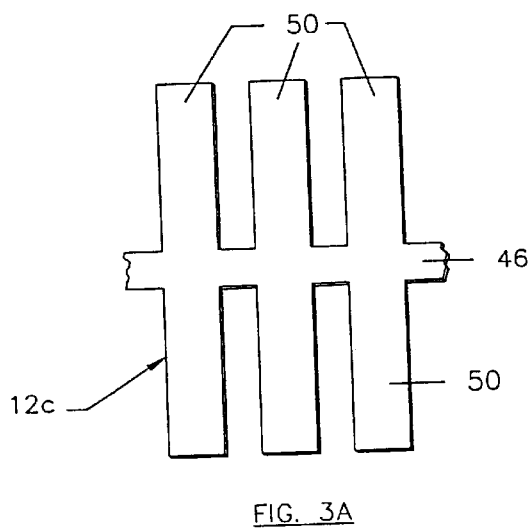
FIG. 3A is a plan illustration of the pattern of flat sheet to form the embodiment of FIG. 3.

FIG. 3 illustrates another embodiment of the invention in which a tubular stent 10c is formed from a sheet 13b having been configured to the flat pattern shown in FIG. 3A. That pattern includes an elongate strip 46 that will serve as a spine for the cylindrical stent and a plurality of extending arms 50. In this embodiment, the ends of the opposed arms 50 are configured to overlap each other as indicated and can be secured in their overlapping regions as by welding or adhesive techniques. The overlapping ends of the extending arms 50 can be configured, as described below in connection with further embodiments, to form a joint having the same thickness as the non-overlapped portions of the arms 50.

Figure 4:
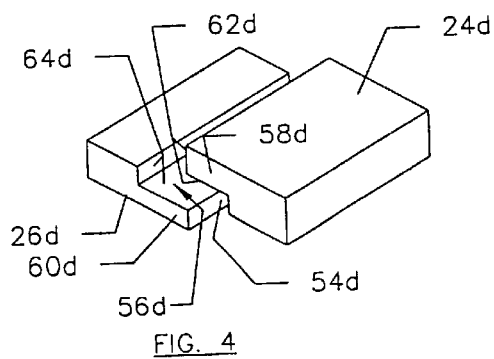
FIG. 4 is an isometric, fragmented and sectional illustration of a segment of the spine of a stent in which the longitudinal margins of the sheet are arranged in an overlap joint to form the spine.
Figure 4A:
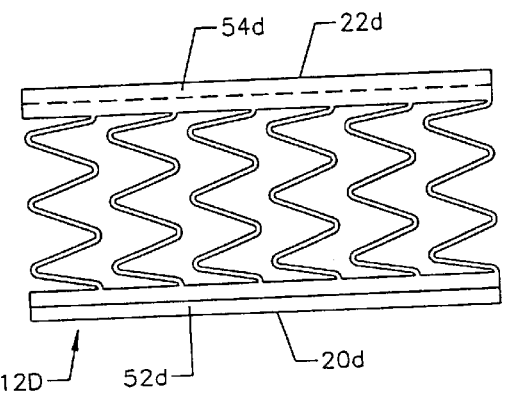
FIG. 4A is a diagrammatic illustration of a flat sheet formed with longitudinal edges adapted to overlap and form the configuration of FIG. 4.
Figure 7B:
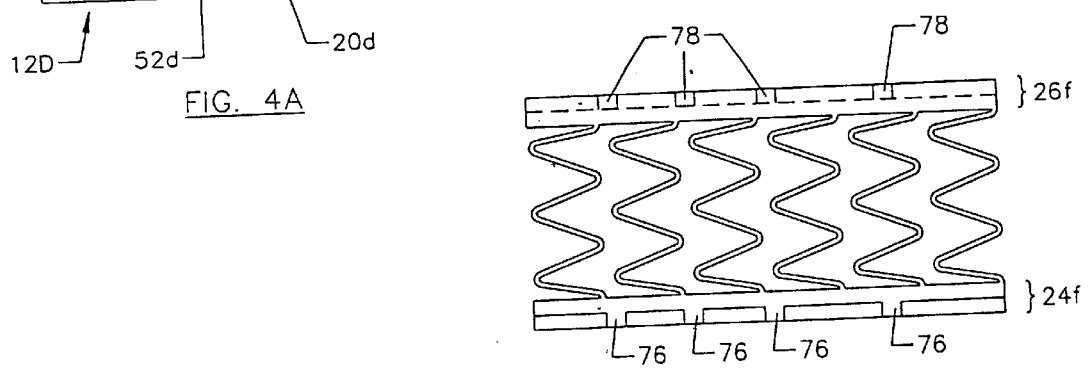
FIG. 7B is an illustration of the flat pattern from which the embodiment of FIG. 7 may be formed.
Figure 5A:
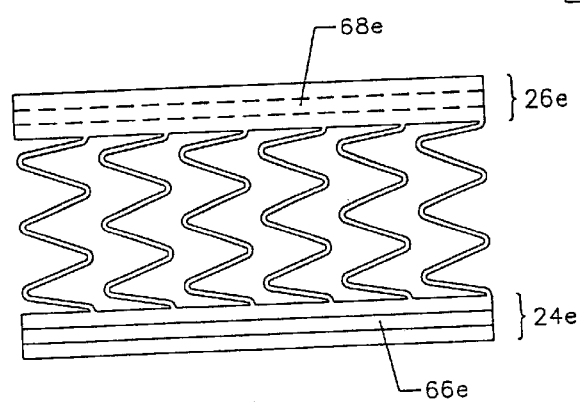
FIG. 5A is an illustration of a flat sheet adapted to form a cylindrical stent as suggested in FIG. 5.

FIG. 4 shows a fragment of the spine in another embodiment of the invention in which the longitudinal edges 20d, 22d and margins 24d, 26d are configured to mate in an overlap. To that end, the sheet 12D (see FIG. 4A) is coated with etchant-resistant film in a pattern that exposes longitudinal strip portions 52d, 54d that extend along each of the longitudinal edges 20d, 22d. The exposed strips are formed so that one, indicated at 52d in FIG. 4A, extends along the longitudinal edge 20d on the inner surface and the other strip 54d extends along the longitudinal edge 22d on the outer surface of the sheet 12D. When the sheet 12D is exposed to the etchant, the exposed strips 52d, 54d will result in formation of longitudinal shoulders 54d, 56d that define half-thickness longitudinal strips 58d, 60d. The widths of the half-thickness strips are essentially equal so that the shoulders 54d, 56d can mate and define a smooth joint having the same combined thickness as the other portions of the stent. The half-thickness of the strips 58d, 60d results from that region of the longitudinal margins being exposed to etchant only on one side. The expandable portion of the sheet, defined by the pattern 14 is etched from both sides of the sheet, the patterns 14 on the inner and outer surfaces of the sheets being in registry. Consequently, in the time it takes for the etchant to remove the half-thickness of the sheet in the region of the strips 52d, 54d, the portion 14 of the sheet will have been removed in the desired pattern through the full thickness of the sheet.

It should be understood that the illustration in FIG. 4 is intended merely to depict the geometry of the juncture of the marginal segments 24d, 26d and illustrates the joint with the half thickness strips 58d, 60d being less than fully overlapped in order to better illustrate the geometric relation of the parts. When the etched sheet 12D is rolled into its cylindrical configuration, the facing surfaces 62d, 64d are brought into full engagement with each other to close the joint. The joint may be secured by any suitable technique such as laser welding, suitable adhesives or the like. It will be appreciated, therefore, that the overlap arrangement and engagement of the facing surfaces 62d, 64d facilitates proper registration of the longitudinal edges 20d, 22d that, in turn, assures proper alignment of the stent cylinder. The nesting of the marginal segments 24d, 26d, enables the stent to have uniform wall thickness fully about its circumference and facilitates nesting of the marginal segments to promote selfalignment of the marginal segments. That facilitates and simplifies assembly of the stent 10.

Figure 5:
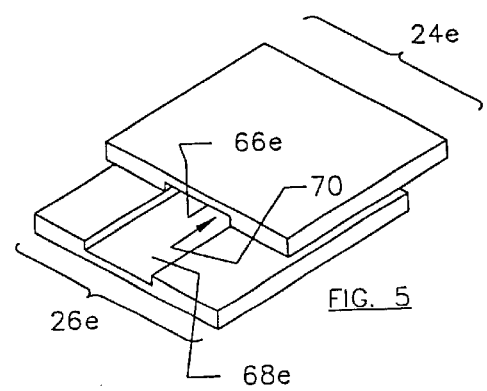
FIG. 5 is an illustration similar to FIG. 4 of another embodiment of the stent in which the connected margins cooperate to define a longitudinal channel receptive to adhesive or a keying member.
Figure 6:
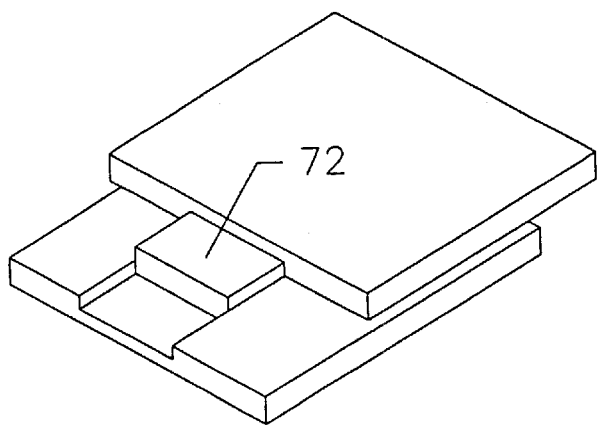
FIG. 6 is an illustration similar to FIG. 5 with the channel containing a longitudinal key.

FIG. 5 illustrates another embodiment of the invention in which the marginal segments 24e, 26e are provided, on opposite sides of the sheet 12, with longitudinal grooves 66e, 68e. The grooves are arranged so that when the sheet 12 is rolled into its cylindrical stent configuration, the grooves will cooperate to define an enclosed channel 70. The channel 70 is adapted to receive a bonding material, such as a suitable adhesive. The adhesive material may be formed from or filled with a radiopaque material so that that portion of the stent will be visible readily under fluoroscopy or X-ray. The bonding material, when solidified, also may serve as a keying element to assure proper relative alignment of the marginal segments 24e, 26e and, therefore, proper alignment of the cylindrical stent. In an alternate of this embodiment, shown in FIG. 6, the bonding material may be replaced by a metallic strip 72 that may itself be from a radiopaque material. The strip 72 is captured in the channel 70 and the components in this embodiment may be secured by any suitable technique as described above.

Figure 7:
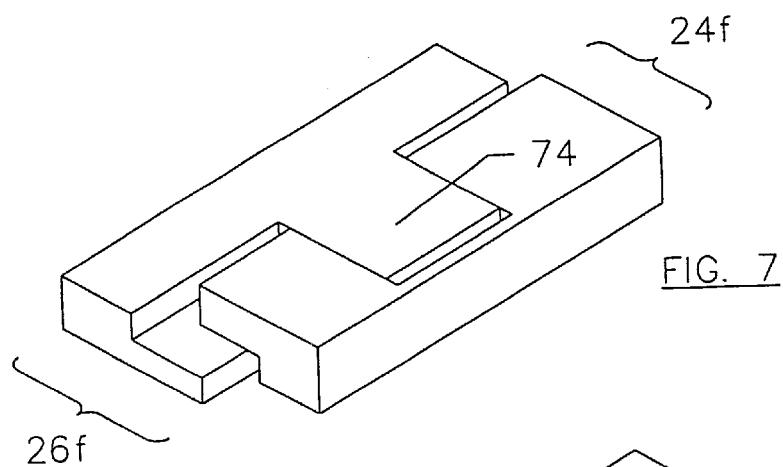
FIGS. 7 and 7A are illustrations of a segment of the connected longitudinal edges of a cylindrical stent formed from a flat sheet of material in another embodiment of the invention.
Figure 7A:
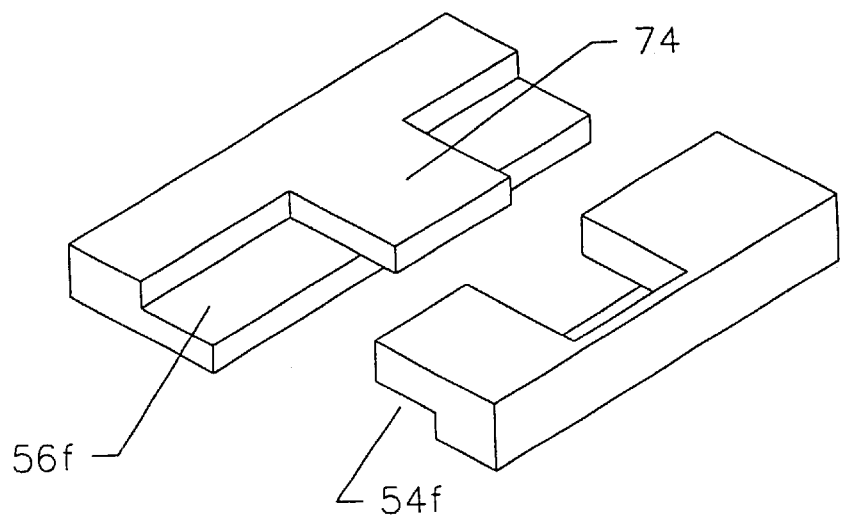

FIG. 7 illustrates another embodiment in the form of a modification to the embodiment illustrated in FIG. 4. In this embodiment, the marginal segments 24f, 26f include the overlap arrangement described in connection with FIG. 4 but with the shoulders 54f, 56f being discontinuous along the length of the sheet 12. In this embodiment, the shoulders are interrupted by transversely extending fingers 74 formed at one or more locations along one of the marginal segments 26f. Each finger 74 extends in a transverse direction and is disposed on the opposite side of the sheet than that of its associated half thickness longitudinal strip. The finger 74 also is formed to include only the half-thickness of the sheet. It is formed by modifying the pattern of etchant-resistant coating along the marginal segments 24f, 26f to interrupt the strip of removed etchant with segments 76 of etchant resistant coating. The segments of etchant-resistant coating will preclude etching of that portion of the marginal segment on one side of the sheet. The opposite side of the sheet, however, will be free of coating in corresponding regions 78 so that half the thickness of the opposite side will be etched away. A complementary pattern is formed on the other side of the other marginal segment so that when the sheet so formed is wrapped into its cylindrical configuration, the marginal segments will nest with each other, as illustrated in FIGS. 7 and 7A to provide a uniform continuous single thickness seam. The marginal segments, so nested, can be secured to each other as described above. The interlocking of the half-thickness longitudinal strips and the transversely extending fingers and grooves further assures registration with additional precision and adds further strength to the joint.

Figure 8:
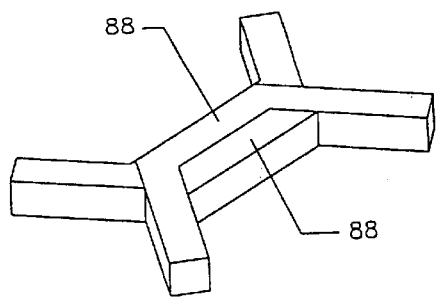
FIG. 8 is an illustration of another embodiment of the invention in which the longitudinal margins of the flat sheet are formed to interlock.

FIG. 8 illustrates another embodiment of the invention in which the marginal segments 24, 26 are formed to define a cooperative interlocking arrangement that resists relative movement of the engaged longitudinal segments longitudinally as well as circumferentially in response to forces developed during balloon expansion of the stent. In this embodiment, the marginal segments 24g, 26g are provided with mutually interlocking segments having engageable surfaces that, when interlocked, prevent longitudinal as well as circumferential movement of the interlocked portion. In the embodiment shown, the marginal segments 24g, 26g are configured so that when assembled in a cylindrical configuration portions of the marginal segments 24g, 26g will overlap each other in selected regions and where those selected regions each will be defined by a half-thickness of sheet material. When the overlapped portions are interlocked, the mating half-thickness regions will define a single thickness juncture.

In the specific embodiment shown, the sheet 12G may be formed to include any desired radially expandable pattern, depicted schematically by the phantom zigzag elements at 14g. The marginal segments 24g, 26g defined along the longitudinal edges 20, 22 of the stent may be formed to include a longitudinally repetitive pattern of alternating transversely projecting regions 80g 82g and recessed regions 84g, 86g. The projecting regions 80g, 82g along one marginal segment are longitudinally aligned with the projecting regions on the other marginal segment. The recessed regions similarly are longitudinally aligned. When the sheet 12G is formed into a cylindrical configuration, the projecting regions along one of the marginal segments will overlie the projecting regions on the other of the marginal segments. The regions of overlap are provided with grooves having a depth equal to one-half of the thickness of the sheet 12 so that when they overlap they will mate and form a unified single thickness joint.

Figure 8A:
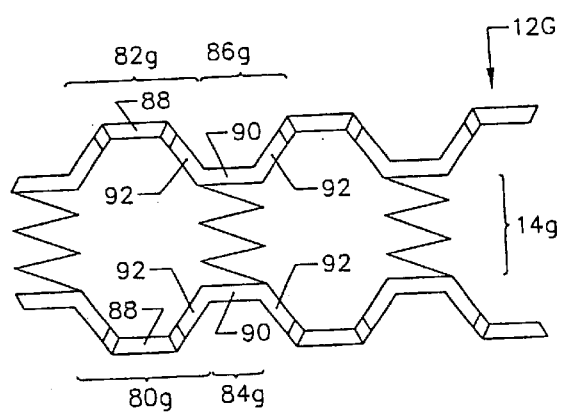
FIG. 8A is an illustration of a flat sheet from which the embodiment of FIG. 8 may be formed.

The specific arrangement shown in FIGS. 8 and 8A may be considered as having marginal segments in which each pair of projecting and recessed regions is defined by alternating outer longitudinal members 88 and inner longitudinal members 90 connected by intermediate diagonally oriented members 92. In this embodiment, when the sheet 12 is formed to its cylindrical configuration, the outer longitudinal members 88 of one of the marginal segments will lie inside of and alongside its associated outer longitudinal member 88 on the other marginal segment. The region of overlap, shown here as adjacent the juncture of the diagonal members 92 with the outer longitudinal members 88 are formed to define recesses that will interlock as shown to define a single thickness joint. The components may be joined by appropriate welding or bonding techniques. It should be appreciated, however, that the structural inter engagement of the components in this embodiment provides additional resistance both to longitudinal and circumferential movement of the joined parts.

From the foregoing, it will be appreciated that the invention provides stent structures and assembly techniques for such stents by which those assembly techniques can be simplified and facilitated. The invention is adaptable to a wide variety of stent configurations. The above-described embodiments can be combined with each other as desired as well as with other stent patterns capable of being formed in a sheet and shaped to a tubular stent. It should be understood, however, that the foregoing description of the invention is intended merely to be illustrative thereof and that other modifications, embodiments and equivalents thereof may be apparent to those skilled in the art.

Having thus described the invention, what I desire to claim and secure by Letters Patent is:

1. A process for forming a stent comprising:

providing a sheet of material having a pattern of interconnected portions that define a plurality of openings through the thickness of the sheet, the sheet having longitudinal margins adapted to overlap when the sheet is rolled into a tubular configuration;

providing a pattern of interlocking projecting and relieved surfaces along the overlapping margins;

forming the sheet into a tube with the interlocking projecting and relieved portions in engagement with each other; and securing the margins of the stent to each other to maintain the tubular stent configuration.

2. A method for forming a stent comprising:

providing a sheet with a pattern of holes defined by a plurality of interconnected members, the sheet having longitudinally extending margins and being adapted to be configured in the tubular configuration with the longitudinal margins overlapped;

forming grooves in the facing surfaces of the overlapped margin so that the grooves can be registered to define an internal channel between the overlapped margins; and locating a material within the channel.

3. A method as defined in claim 1 wherein the material is radiopaque.

4. A method as defined in claim 1 wherein the material serves as a key to interlock the overlapped margins.

* * * * *

UNITED STATES PATENT AND TRADEMARK OFFICE
CERTIFICATE OF CORRECTION

PATENT NO.      : 6,350,279 B1                                                                   Page 1 of 1
DATED           : February 26, 2002
INVENTOR(S)     : Colm P. McGuiness It is certified that error appears in the above-identified patent and that said Letters Patent is hereby corrected as shown below:

Column 8,
Line 44, delete "claim 1" and insert -- claim 2 -- therefor.
Line 46, delete "claim 1" and insert -- claim 2 -- therefor.

Signed and Sealed this

Fifth Day of November, 2002

Attest:

Attesting Officer

JAMES E. ROGAN
*Director of the United States Patent and Trademark Office*